(12) United States Patent
Lepareur et al.

(10) Patent No.: US 9,579,409 B2
(45) Date of Patent: Feb. 28, 2017

(54) COMPOSITION FOR THERAPEUTIC USE, INCLUDING AN ORGANIC LIPID PHASE AND A RARE-EARTH RADIOISOTOPE COMPLEX

(71) Applicants: CENTRE EUGENE MARQUIS, Rennes (FR); ECOLE NATIONALE SUPERIEURE DE CHIMIE, Rennes (FR); UNIVERSITE DE RENNES I, Rennes (FR)

(72) Inventors: Nicolas Lepareur, Vern-sur-Seiche (FR); Etienne Garin, La Meziere (FR); Nicolas Noiret, Saint-Sulpice-la-Foret (FR); Valerie Ardisson, Rennes (FR)

(73) Assignees: CENTRE EUGENE MARQUIS, Rennes (FR); ECOLE NATIONALE SUPERIEURE DE CHIME, Rennes (FR); UNIVERSITE DE RENNES I, Rennes (FR)

( * ) Notice: Subject to any disclaimer, the term of this patent is extended or adjusted under 35 U.S.C. 154(b) by 0 days.

(21) Appl. No.: 14/415,282

(22) PCT Filed: Jul. 17, 2013

(86) PCT No.: PCT/EP2013/065131
§ 371 (c)(1),
(2) Date: Jan. 16, 2015

(87) PCT Pub. No.: WO2014/012997
PCT Pub. Date: Jan. 23, 2014

(65) Prior Publication Data
US 2015/0202334 A1 Jul. 23, 2015

(30) Foreign Application Priority Data
Jul. 18, 2012 (FR) ..................... 12 56951

(51) Int. Cl.
| | | |
|---|---|---|
| *A61P 35/00* | (2006.01) | |
| *A61K 103/32* | (2006.01) | |
| *A61K 103/30* | (2006.01) | |
| *A61K 51/04* | (2006.01) | |
| *A61K 51/12* | (2006.01) | |

(52) U.S. Cl.
CPC ...... *A61K 51/0497* (2013.01); *A61K 51/0404* (2013.01); *A61K 51/0478* (2013.01); *A61K 51/1217* (2013.01)

(58) Field of Classification Search
CPC ...... C08L 83/04; C08L 2666/52; C08L 83/00; A61K 51/04; A61K 51/1203; A61K 51/0404; A61K 51/0497; A61K 51/0474; A61K 47/48753; A61K 51/0478; A61K 8/0291; A61K 8/0295; A61K 8/14; A61K 8/33; C07F 7/00; C07F 7/006
See application file for complete search history.

(56) References Cited

FOREIGN PATENT DOCUMENTS

| WO | WO92/04338 | * | 8/1991 | ......... C07D 295/116 |
| WO | 2011101436 A1 | | 8/2011 | |

OTHER PUBLICATIONS

Urizzi, P. et al. "Attachment of radiometals to LDL with lipid analogues of EDTA or DTPA type complexing agents. Comparison of two labelign procedures", Journal de chimie Physique, Societe de chimie physique, vol. 94, No. 2, Jan. 1997. pp. 371-375.*
Urizzi et al. (Radiometals to LDL with 1 pi d analogues of EDTA or DTPA type complexing agnets, Comparison of two labeling procedures, Journal de Chimie Physique, Societe de Chimie Physique, vol. 94, No. 2, Jan. 1997.*
Yu et al. ("Y-oxine-ethiodol, a potential radiopharmaceutical for the treatment of liver cancer", Applied Radiation and Isotopes, Elsevier, Oxford, GB, vol. 58, No. 5, May 2003, pp. 567-573, cited in IDS filed Apr. 1, 2015 and supplied by Applicant in File Wrapper).*
P. Urizzi et al: radiometals to LDL with 1 i pi d analogues of EDTA or DTPA type complexing agents. Comparison of two labeling procedures. Journal De Chimie Physique. Societe De Chimie Physique. Paris. FR. vol. 94. No. 2. Jan. 1, 1997. pp. 371-375.
Yu Jet al: "Y-oxine-ethiodol. a potential radiopharmaceutical for the treatment of liver cancer". Applied Radiation and Isotopes. Elsevier. Oxford. GB. vol. 58. No. 5. May 1, 2003. pages 567-573.
Subramanian Suresh et al: "Preparation of Lu-177-Labeled Oxine in Lipiodol as a Possible Agent for Therapy of Hepatocellular Carcinoma: A Preliminary Animal Study". Cancer Biotherapy & Radiopharmaceuticals. vol. 25. No. 5. Oct. 2010. pp. 539-543.
Das Tapas et al: "Preparation of 166Ho-oxine-lipiodol and its preliminary bioevaluation for the potential application in therapy of liver cancer.". Nuclear Medicine Communications May 2009. vol. 30. No. 5. May 2009. pp. 362-367.
Jianlin Y et al: "Raman spectroscopic studies on tropolone complexes with La. Nd. Sm. Yb". Spectrochimica Acta. Part A: Molecular and Biomolecular Spectroscopy. Elsevier. Amsterdam. NL. vol. 64. No. 4. Jul. 1, 2006. pp. 1072-1076.
B. Lambert, Re-HDD/Lipidol Therapy for Hepatocellular Carcinoma: A Phase I Clinical Trial; J.Nucl.Med., 2005, 46, 60-66); 7 pages.
P.Y. Mu et al., "Research on extracted Y with P204 in lipiodol for liver cancer"; J. Radioanal. Nucl. Chem., 2007, 272, 669-671.
S.J. Oh et al., "Automated of the synthesis of highly concentrated Re-MAG for intracoronary radiation therapy"; Appl. Radiat. Isot., 30 2001, 54, 419-427.
S.J. Oh et al., "Automated preparation of Re-labeled radiopharmaceuticals for endovascular radiation therapy" Appl. Radiat. Isot., 2003, 59, 225-230).

* cited by examiner

*Primary Examiner* — Audrea Buckley
(74) *Attorney, Agent, or Firm* — Thomas | Horstemeyer, LLP

(57) ABSTRACT

The invention relates to a therapeutic composition including a complex having the following formula (1), including a rare-earth radioisotope in ionic form, said complex being solubilized in an organic lipophilic phase: $[M(L)_3]$ in which: M denotes the rare-earth radioisotope in ionic form, and L denotes a tropolone ligand or a ligand derived from tropolone.

5 Claims, 1 Drawing Sheet

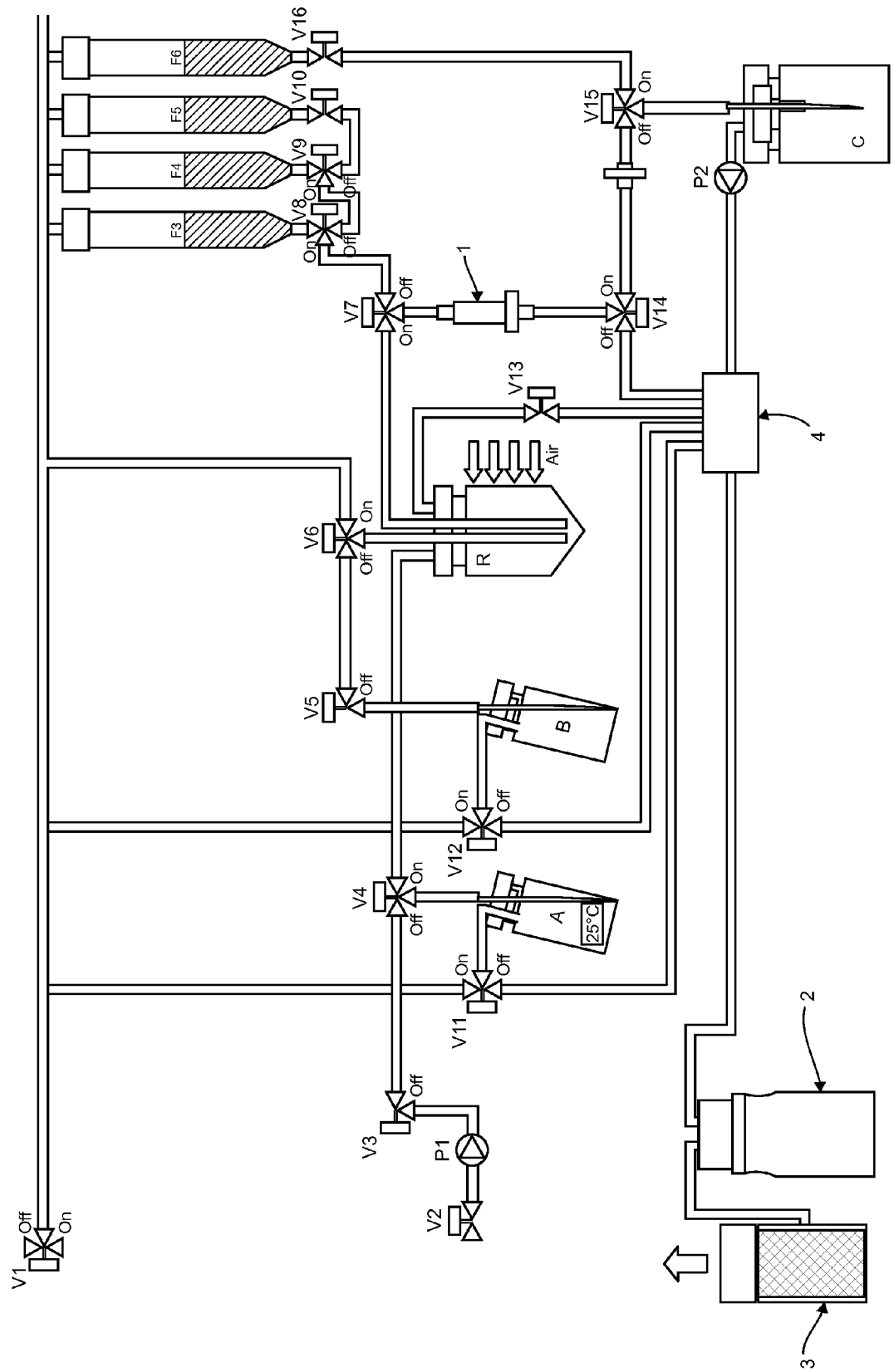

COMPOSITION FOR THERAPEUTIC USE, INCLUDING AN ORGANIC LIPID PHASE AND A RARE-EARTH RADIOISOTOPE COMPLEX

CROSS-REFERENCE TO RELATED APPLICATION

This application is the 35 U.S.C. §371 national stage of PCT Application No. PCT/EP2013/065131, filed Jul. 17, 2013, which is herein incorporated by reference in its entirety and which also claims priority to, and the benefit of, French Patent Application No. 1256951, filed Jul. 18, 2012, which is herein incorporated by reference in its entirety.

1. FIELD OF THE INVENTION

The field of the invention is that of the formulation of compositions for therapeutic use among humans.

More specifically, the invention pertains to a composition comprising a lipid organic phase and a rare-earth radioisotope complex.

2. PRIOR ART

Liver cancer among humans is a serious pathology that represents the world's fifth most common cancer. Its incidence varies greatly according to the world's different regions. It affects most particularly South-East Asia and Africa but its incidence in the developed countries and especially Europe is greatly increasing (E. Garin, P. Bourguet, in Ell and Gambir 3rd Ed., *Nuclear Medicine in Clinical Diagnosis and Treatment*, Hong-Kong: Churchill-Livingstone, 2004, 473-483).

The prognosis is extremely poor. Therapeutical possibilities are limited by the degree of a severity of the underlying hepatopathy and by the intra-hepatic extension of the disease. Liver transplant is the only truly curative treatment for the tumor and the predisposing liver disease. Surgical resection is also an efficient surgical method. Unfortunately, it can only be applied to non-cirrhotic patients who represent about 5% of cases in western countries. In this context, two therapeutic approaches seem to be the most promising— metabolic radiotherapy by intra-arterial or intra-tumoral channels and arterial chemoembolization.

Metabolic radiotherapy is widely used in the curative or palliative treatment of numerous cancers, and especially in liver cancer. The metabolic radiotherapy of hepatic tumors is done chiefly through the hepatic artery. The healthy liver is irrigated with blood and oxygen both through the portal vein and the hepatic artery. However, in the case of tumors, these veins and arteries, which are highly vascularized, are essentially irrigated by the hepatic artery while the healthy tissues are irrigated to 80% by the portal vein.

Arterial chemoembolization was developed in order to improve the performance of metabolic radiotherapy. In this technique, a mixture is injected into the patient's hepatic artery, containing a chemotherapeutic substance associated with particles that provoke an embolism, i.e. they block the blood flow towards the tumor.

This therapy, which is an alternative to surgical resection and radiotherapy, has a twofold advantage:

it enables the release of a highly concentrated dose of chemotherapeutical substance into the tumor while sparing healthy tissues and the rest of the organism, the embolism of the tumor blocks the medicine therein, increasing its efficacy while weakening the tumor by depriving it of nutrients and oxygen.

In addition, the secondary effects for the patient are greatly limited and this therapy seems to give an advantage in terms of survival to patients treated by this method (B. Lambert, *J. Nucl. Med.*, 2005, 46, 60-66).

The vehicle most used for intra-hepatic administration is Lipiodol. Lipiodol also known as Ethiodiol® in the United States is a liposoluble contrast agent obtained by iodization and esterification of poppy-seed oil (a mixture of linoleic, oleic, palmitic and stearic acids). The proportion of iodine is about 38% by mass (i.e. 475 mg/mL). Lipiodol is selectively picked up by hepatic carcinomas (HCC) and by certain hepatic metastases of colonic, neuroendocrinal and mammary origin. Lipiodol has therefore been used to detect hepatic carcinoma and its possible satellite tumors, which are non-detectable by the usual methods of imaging, and then also to convey chemotherapeutical substances. It has also been shown that there is an intra-tumoral retention time far greater than the retention time in the healthy liver, with retention in hepatic carcinoma that could go up to several months. The persistence of Lipiodol in tumors has led to the proposing of a covalent labeling of Lipiodol by radioactive iodine-131 ($^{131}$I) in order to carry out a targeted radiotherapy, the "cold" iodine, i.e. the non-radioactive iodine contained in Lipiodol being replaced by radioactive iodine. However, the lifetime of iodine-131 ($^{131}$I) is only eight days and this element is a source of major emission of γ radiation. Therefore, the interest in developing Lipiodol in routine clinical therapy has rapidly declined.

Besides, since the properties of iodine-131 are sub-optimal, other radio elements with more suitable characteristics have been proposed, especially yttrium-90 ($^{90}$Y) and rhenium-186 or 188 ($^{186}$Re, $^{188}$Re). However, yttrium-90 is costly and difficult to image and the risk of release, leading to undesirable medullary radiation exposure, cannot be overlooked. This limits its development (S. J. Wang et al., *J. Nucl. Med.*, 1996, 37, 332-335).

With regard to yttrium, two labeling strategies have been described. The first which is similar to Iodine-131 marking, consists of a covalent labeling of Lipiodol (S. J. Wang et al., J. Nucl. Med., 1996, 37, 332-335.), via an EDTB chelate (N,N,N',N'-tetrakis(2-benzymidazoylmethyl)1,2-ethanediamine). However, this technique has proved to be impracticable and non-reproducible.

The second strategy, which is currently the most developed one, consists of the solubilization in Lipiodol of a chemically neutral and lipophilic complex of yttrium. According to the literature, two lipophilic complexes have been described to label Lipiodol, 8-hydroxyquinoline or oxine (J. Yu et al., Appl. Radiat. Isot., 2003, 58, 567-573.) and di(2-ethylhexyl) orthophosphoric acid or P204 (P. Y. Mu et al., J. Radioanal. Nucl. Chem., 2007, 272, 669-671.). With regard to the complex P204, no information on its structure, biodistribution, toxicity and stability is available at present. Lipophilic complexes of lutetium and holmium based on oxine have also been described (S. Subramanian et al., Cancer Bioth. Radiopharm., 2010, 25, 539-543; T. Das et al., Nucl. Med. Commun., 2009, 30, 362-367). However, the oxine-based complexes are highly unstable: the rare-earth ions get detached very rapidly from the oxine complex and get fixed predominantly in the bones.

In addition, the preparation of radiotracers, and especially the labeling of Lipiodol, causes non-negligible radiation exposure on the part of the handling personnel. In this context, several automated systems have been described in the literature, chiefly for the preparation of fluorine and carbon radiotracers for imaging by positron emission tomography (PET), but also for the preparation of rhenium-based tracers, the activity of which is greater than 15 GBq (S. J. Oh et al., *Appl. Radiat. Isot.*, 2001, 54, 419-427; S. J. Oh et al., *Appl. Radiat. Isot.*, 2003, 59, 225-230).

In this context, we have developed a new lipophilic complex of rare-earth radioisotope enabling the easy labeling of Lipiodol based on tropolone or on a tropolone derivative.

3. GOALS OF THE INVENTION

The invention is aimed especially at overcoming these drawbacks of the prior art.

More specifically, it is a goal of the invention, in at least one embodiment, to provide a stable radiolabeled lipophilic complex.

It is another goal of the invention, in at least one embodiment, to implement a method of manufacture of these complexes that reduces the risks of radiation for the handler.

It is yet another goal of the invention, in at least one embodiment, to provide a lipophilic complex providing a composition for treating liver cancer in humans.

4. SUMMARY OF THE INVENTION

These goals as well as others that shall appear here below are achieved by means of a therapeutical composition, comprising a complex having the following formula (1) comprising a rare-earth radioisotope, said complex being solubilized in a lipophilic organic phase:

$$[M(L)_3] \quad (1)$$

wherein:
M designates the rare-earth radioisotope, and
L designates a tropolone ligand or a tropolone-derived ligand.

Thus, the invention relies on a wholly novel and original approach to combining the properties of the rare-earth radioisotopes with a lipophilic organic phase, said organic phase enabling these rare-earth radioisotopes to be conveyed to the pathological cells. Thus, therapies by chemo-embolization, using this composition are more efficacious. The rare earths are complexed in ion form with the ligand, enabling the labeling of the lipophilic organic phase. Now, complexes formed by a rare-earth radioisotope in ion form and a tropolone or tropolone-derived ligand are particularly stable.

The lipophilic organic phase can be an organic solvent or an oil. Should the organic phase be an oil, it will preferably be a mixture of iodized fatty acid esters.

The term "rare earth" applies to the chemical family of lanthanides, to which we may add scandium and yttrium. These elements have similar chemical properties. Thus, they can easily be interchanged to form complexes of comparable structures. More specifically, the term "rare-earth radioisotope" designates an element chosen preferably from the group formed by $^{47}$Sc, $^{90}$Y, $^{140}$La, $^{139}$Ce, $^{142}$Pr, $^{143}$Pr, $^{145}$Pr, $^{149}$Pm, $^{153}$Sm, $^{149}$Eu, $^{150}$Eu, $^{159}$Gd, $^{149}$Tb, $^{161}$Tb, $^{165}$Dy, $^{166}$Dy, $^{161}$Ho, $^{166}$Ho, $^{169}$Er, $^{167}$Tm, $^{170}$Tm, $^{173}$Tm, $^{175}$Yb, $^{176m}$Lu, $^{177}$Lu, $^{179}$Lu.

Advantageously, L is chosen from amongst halogenotropolone, α-methyltropolone, β-methyltropolone, γ-methyltropolone, α-isopropyltropolone, β-isopropyltropolone, γ-isopropyltropolone, nootkatin, stipitatic acid, puberulic acid, puberulonic acid, purpurogallin, colchicine or a derivative of these substances, L preferably designating β-isopropyltropolone. The tropolone ligands and their derivatives, especially β-isopropyltropolone, form particularly stable complexes with rare earths. Thus, the phenomenon according to which the rare earth ions get separated from their ligand and get fixed anarchically to the organs is avoided or at least considerably diminished.

According to one particularly advantageous embodiment, M is chosen from among $^{90}$Y, $^{47}$Sc, $^{177}$Lu, $^{166}$Ho. These elements have particularly valuable properties for the treatment of tumors.

Preferably, said lipophilic organic phase is Lipiodol®. Lipiodol is a mixture of iodized methyl esters of poppyseed oil. The use of Lipiodol® in a composition according to the present invention gives a stable composition. In addition, it is characterized by a preferential and sustained tumor fixation, thus enabling the efficacious treatment of liver cancer.

In one advantageous embodiment, said lipophilic phase is put into emulsion in an aqueous phase, said aqueous phase preferably being a physiological serum. This improves its biodistribution and enables the formulation of injectable compositions well-tolerated by humans.

An object of the invention is also a method of manufacture comprising the steps of:
a. one-step synthesis of the complex having formula (1),
b. column purification of the complex having the formula (1),
c. evaporation of the organic solvent at a temperature of 40° C. to 100° C.,
d. sterilizing filtration,
e. solubilizing the complex having the formula (1) in said lipophilic organic phase.

The composition according to the invention can be easily prepared manually.

However, the composition according to the invention comprising a rare-earth radioisotopic complex having formula (1) and the lipophilic organic phase can also be prepared by means of an automated system. The automation of the method of synthesis according to the invention limits radiation exposure on the part of the handlers through radioactivity while enabling the production of the composition of the invention reproducibly and with high efficiency.

Advantageously, the one-step synthesis of the complex having formula (1) is done using a precursor having the following formula (2):

$$MZ_3 \quad (2)$$

where M designates a rare-earth radioisotope and Z is a halogenic anion, a nitrate anion, a triflate anion or an acetate anion.

In one-step synthesis, the complex $MZ_3$ is mixed with a solution of ligand with stirring, at ambient temperature. A solvent enabling the elimination of the anion Z is then added to the mixture. After centrifugation or column liquid-solid separation, the phase containing on the one hand the solvent and the complex $[M(L)_3]$ and, on the other hand, the aqueous phase containing anion Z, are separated.

The purification is done by chromatography, especially by liquid-solid extraction (SPE). The column purification can be done on a column C8 or again on a column C18. The terms column C8 or C18 are understood to be Sep-Pak® type reverse-phase columns for which the stationary phase is an apolar phase constituted by silica gel on which 8-atom or 18-atom carbon chains are grafted. In this case, the elution is done by using a polar mobile phase and is chosen as a function of the chemical nature of the molecules to be eluted. The residual solvent is evaporated by heating at a temperature of 40° C. to 100° C.

After elution, the purified complex undergoes sterilizing filtration and is then solubilized in 2 to 3 ml of non-radioactive Lipiodol®. The term "sterilizing filtration" is understood to mean the passage of the complex in solution through a filter with a porosity of 0.2 μm to eliminate the pathogenic microorganisms.

The automation of the method enables a use of this formula for clinical and pharmaceutical purposes while greatly restricting the exposure of the handler to radioactivity. Thus, the method according to the present invention makes it possible, as compared with the prior art, to obtain stable, efficacious compounds compatible with concrete therapeutical use.

In on advantageous embodiment, the method according to the invention furthermore comprises a final step of nano-encapsulation. Thus, the composition according to the invention can be administered orally or by injection. The nature of the capsule depends on the physiological target to be reached. In addition, it is possible to graft, onto the surface of the nano-capsules, antibodies or specific peptides of tumors in order to improve the targeting. For example, somatostatin analogs for the treatment of neuroendrocrinal tumors can be grafted. The composition according to the invention, once encapsulated, can also be applied in the treatment of gliomas.

Another aspect of the invention relates to the use of the composition for the treatment of liver cancer among humans. The composition is characterized by a preferential and sustained tumoral fixation, thus enabling the efficacious treatment of liver cancer. It therefore enables the treatment of different forms of liver cancer, whatever their etiology and their histology (hepatocarcinoma, cholangiocarcinoma, hepatic metastasis, etc).

5. DESCRIPTION OF ONE EMBODIMENT OF THE INVENTION

The general principle of the invention relies on the labeling of a lipophilic organic phase by an organic complex bearing a rare-earth radioisotopic ion, the lipophilic organic complex being a vector of choice to convey the radioisotopic complex to the cancerous cells and the radioisotope label enabling the specific destruction of the pathological cells.

The following embodiments are given by way of examples of the present invention and in no way constitute a limitation thereof. FIG. 1 is the diagram of the automated method.

EXAMPLE 1

Preparation of the Complex $^{90}$Y-Tropolone by Extraction According to the Manual Method In an appropriate recipient, 1 ml of yttrium-90 ($^{90}$Y) chloride, having a radioactivity of 0.8 mCi, is mixed with 1 mL of a $10^{-2}$ mol/L tropolone solution in a PBS (phosphate buffered saline, pH 7.4) buffer. After 5 minutes of stirring at ambient temperature, 2 mL of chloroform are added and the phases are separated by centrifugation. The organic phase is collected.

The labeling efficiency in percentage is computed as follows:

Labeling efficiency(%)=[activity of the lipophilic phase($Bq$)×100]/[activity of the lipophilic phase ($Bq$)+activity of the aqueous phase($Bq$)]

The radiochemical purity compatible with a pharmaceutical application is defined as at least 90% of the complex M(L)$_3$ contained in the lipophilic phase.

Thin-layer chromatographic (TLC) analysis on Whatman paper seeks to determine the radiochemical purity of the prepared solution. The eluent used to carry out the migration is methanol. The chromatography is then carried out according to methods well known to those skilled in the art. Briefly, a drop of radiolabeled solution is deposited on a TLC strip, which is then placed in a development chamber. A solvent, in this case methanol, is disposed in the tank without touching the deposition point. The chamber is closed and the migration of the solvent front takes place, carrying with it the sample of radiolabeled solution. At the end of the migration, the strip is deposited by revelation and viewed on a photo-imaging plate, for example by means of the Cyclone phosphor-imager by Perkin-Elmer.

The radiochemical purity (RCP) is expressed in percentage and computed as follows:

RCP=[activity of the radioactive spot of interest ($Bq$)×100]/[total activity($Bq$)]

The ratio of migration by radioactivity Rf=(radioactivity of the migration front of the solvent carrying the compound ($Bq$))/(total radioactivity of the TLC strip ($Bq$)).

In this example, the yield is equal to 89.5% and the radiochemical purity (RCP) is equal to 96%.

EXAMPLE 2

Preparation of the Complex $^{90}$Y-β-isopropyltropolone by Extraction According to the Manual Method In an appropriate recipient, 0.5 mL of yttrium-90 ($^{90}$Y) acetate having radioactivity of 1.63 mCi, is mixed with 0.5 mL of a $10^{-2}$ mol/L β-isopropyltropolone solution in ethanol. After 5 minutes of stirring at ambient temperature, 2 mL of chloroform are added and the phases are separated by centrifugation. The organic phase is collected.

Yield=98.3%

Radiochemical purity (RCP)=99.9%

EXAMPLE 3

Preparation of the Complex $^{90}$Y-Tropolone According to the Manual Method

In an appropriate recipient, 1 mL of yttrium-90 chloride having a radioactivity of 1.05 mCi, is mixed with 1 mL of a $10^{-2}$ mol/L tropolone solution, in PBS (pH=7.4). After 5 minutes of stirring at ambient temperature, the solution is purified on two Sep-Pak® C$_{18}$ columns (preliminarily activated by physiological serum), and the complex is eluted by 2 mL of ethanol.

Yield=70%

Radiochemical purity (RCP)=95.1%

EXAMPLE 4

Preparation of the Complex $^{90}$Y-β-isopropyltropolone According to the Manual Method In an appropriate recipient, 0.5 mL of yttrium-90 acetate having radioactivity of 1.4 mCi, is mixed with a 0.5 mL of a $10^{-2}$ mol/L β-isopropyltropolone solution, in ethanol.

After 5 minutes of stirring at ambient temperature, the solution is purified on an Sep-Pak® C8 reverse phase cartridge by 5 mL distilled water. The complex $^{90}$Y-β-isopropyltropolone is eluted from the cartridge by 2 mL of ethanol.

Yield=75%
Radiochemical purity (RCP)=92.7%

EXAMPLE 5

Preparation of the Labeled Compound Marked with $^{90}$Y in Solution in Lipiodol The organic solution obtained in the examples 1 to 4 is evaporated at a temperature of 40° C. to 100° C., and the residue is dissolved in 2 mL of Lipiodol®. The mixture is stirred for 5 minutes. The radiolabeled lipiodolized phase is collected.

EXAMPLE 6

Preparation of the labeled compound with $^{90}$Y in solution in Labrafac™CC

The organic solution obtained in the examples 1 to 4 is evaporated at a temperature of 40° C. to 100° C., and the residue is dissolved in 2 mL of Labrafac™CC (caprylic/capric acid triglycerides). The mixture is shaken for 5 minutes. The radiolabeled lipophilic phase is collected.

EXAMPLE 7

Automated Preparation of the Complex $^{90}$Y-β-isopropyltropolone in Elution in Lipiodol Referring to FIG. 1, a description is provided of the automated preparation of the complex $^{90}$Y-β-isopropyltropolone in solution in Lipiodol®. The automated system comprises a set of flasks containing different reagents as well as reactors in which the chemical reactions occur. The circulation of reagents in the set of flasks in reactors is controlled by a system of valves (V1-V15) and pumps (P1, P2). The automated operation of the valves and pumps is programmed and pre-recorded in a control system 4. An automaton suited to implementing the method according to the invention is of the Taddeo automaton type (Comecer, Italy).

In brief, a volume of 0.5 mL of yttrium-90 chloride having radioactivity of 1.61 mCi and contained in a recipient A is transferred into the reactor R. A volume of 0.5 mL of a $10^2$ mol/L β-isopropyltropolone solution, in ethanol in a recipient B is also transferred into the reactor R. After 5 minutes at ambient temperature, the reaction medium is transferred to a Sep-Pak® C$_{18}$ type column 1 and then washed with 5 mL of distilled water contained in the flask F3. The complex $^{90}$Y-β-isopropyltropolone is then eluted in the flask C by 2.5 mL of ethanol contained in the flask F5. The ethanol is evaporated at 100° C. and under reduced pressure, and 2 mL of Lipiodol® contained in the flask F6 are finally added to give the desired radiolabeled composition. The wastes such as the wash solutions and excess reagents are recovered in a waste container 2. These wastes are especially filtered by a filtration system 3 before being eliminated according to the good laboratory practice.

To improve the progress of the reaction mixture, the water-ethanol mixture contained in the flask F4 can be made to pass through the column. This additional washing depends on the lipophilicity of the ligand used.

Yield=51.6%
Radiochemical purity (RCP)=99.8%

As can be observed, in the light of the results, the automated method according to the invention gives a composition comprising a lipophilic organic phase in which a rare-earth radioisotope complex is solubilized in a manner that is sure for the user, fast and gives excellent radiochemical purity.

EXAMPLE 8

Biodistribution of Lipiodol Labeled by the Complex $^{90}$Y-β-isopropyltropolone, 72 h Post-injection A volume of 0.15 mL, having radioactivity of 53 μCi, of radiolabeled Lipiodol was injected into the hepatic artery of rats having contracted hepatocellular cancer (through an injection of N1S1 cells 16 days earlier). 72 h after injection, the rats were euthanized and their organs were weighed and counted.

| Tested tissue | Injected activity (%) | Injected activity per gram of organ (%) |
| --- | --- | --- |
| Tumor | 30.2 | 13.4 |
| Tumoral liver | 17.1 | 7.6 |
| Healthy liver | 22.2 | 4 |
| Lungs | 1.7 | 0.8 |
| Heart | 0.3 | 0.3 |
| Spleen | 0.4 | 0.9 |
| Kidneys | 4.7 | 2.6 |
| Stomach | 0.7 | 0.2 |
| Intestines | 2.2 | 0.2 |
| Bones (femur) | 1.8 | 1.7 |

As can be observed from the results, the radioactive activity is chiefly in the tumor, the affected liver and the healthy liver. The activity in the healthy liver was nevertheless three times lower than in the tumor, indicating a preferential fixation of the composition according to the invention in the hepatic tumor. The fixing in the other organs was also low. The composition of radiolabeled Lipiodol® through the complex according to the invention therefore makes it possible to specifically target the liver and the hepatic tumor. The problems of anarchic fixation of radioactive complexes are therefore avoided through the composition of the invention, the complex [M(L)$_3$] being particularly stable. The composition according to the invention is therefore more reliable and more efficacious.

The invention claimed is:
1. A therapeutical composition, comprising a complex having the following formula (1) comprising a rare-earth radioisotope, said complex being solubilized in a lipophilic organic phase:

$$[M(L)_3] \quad (1)$$

wherein:
M designates the rare-earth radioisotope, wherein the rare-earth radioisotope is $^{90}$Y or $^{47}$Sc, and
L designates a tropolone ligand or a tropolone-derived ligand chosen from amongst halogenotropolone, α-methyltropolone, β-methyltropolone, γ-methyltropolone, α-isopropyltropolone, β-isopropyltropolone, γ-isopropyltropolone, nootkatin, stipitatic acid, puberulic acid, puberulonic acid, purpurogallin, or colchicine.

2. The therapeutical composition according to claim 1 wherein L is β-isopropyltropolone.

3. The therapeutical composition according to claim 1 wherein said lipophilic organic phase is a mixture of iodized methyl esters of poppyseed oil, containing 38% by mass iodine.

4. The therapeutical composition according to claim 1 wherein said lipophilic phase is put into emulsion in an aqueous phase.

5. The therapeutical composition according to claim 4, wherein said aqueous phase is a physiological serum.

* * * * *